(12) United States Patent
Cho et al.

(10) Patent No.: US 8,981,125 B2
(45) Date of Patent: Mar. 17, 2015

(54) METHOD FOR PREPARING 1,3,5-TRIOXANE

(75) Inventors: In Gi Cho, Gimcheon-si (KR); Jin Sang Choi, Gimcheon-si (KR); Kyung Min Kang, Gimcheon-si (KR)

(73) Assignee: KTP Industries, Inc., Gimcheon-si (KR)

( * ) Notice: Subject to any disclaimer, the term of this patent is extended or adjusted under 35 U.S.C. 154(b) by 0 days.

(21) Appl. No.: 13/882,034

(22) PCT Filed: Aug. 18, 2011

(86) PCT No.: PCT/KR2011/006061
§ 371 (c)(1),
(2), (4) Date: Jun. 7, 2013

(87) PCT Pub. No.: WO2012/057437
PCT Pub. Date: May 3, 2012

(65) Prior Publication Data
US 2013/0261318 A1    Oct. 3, 2013

(30) Foreign Application Priority Data

Oct. 29, 2010  (KR) .................. 10-2010-0107119

(51) Int. Cl.
  C07D 323/06  (2006.01)
  B01D 3/40   (2006.01)
  B01D 3/00   (2006.01)

(52) U.S. Cl.
  CPC ............ C07D 323/06 (2013.01); B01D 3/40 (2013.01); B01D 3/009 (2013.01)
  USPC .......................................... 549/368; 203/14

(58) Field of Classification Search
  CPC .................................................... C07D 326/06
  USPC .......................................... 549/368; 203/14
  See application file for complete search history.

(56) References Cited

U.S. PATENT DOCUMENTS 4,504,670 A * 3/1985 Voigt et al. .................. 549/347
6,433,194 B1 * 8/2002 Schweers et al. ........... 549/368

FOREIGN PATENT DOCUMENTS

| JP | 6-228127 A | 8/1994 |
| KR | 10-2001-0097592 A | 11/2001 |
| KR | 10-2006-0043301 A | 5/2006 |

OTHER PUBLICATIONS

International Searching Authority, International Search Report for PCT/KR2011/006061 dated Apr. 30, 2012.

* cited by examiner

*Primary Examiner* — Andrew D Kosar
(74) *Attorney, Agent, or Firm* — Sughrue Mion, PLLC

(57) ABSTRACT

The present invention relates to a method for preparing 1,3,5-trioxane using a reaction distillation tower including a reactor and integrally formed distillation and extraction sections. Particularly, the present invention relates to a method for preparing 1,3,5-trioxane characterized in that the amount of formaldehyde discharged to the outside of the system is reduced, to thereby increase the yield of 1,3,5-trioxane by recirculating a portion of the water phase, which is discharged through the top of the reaction extraction tower, to the extraction section, and thus to the upper portion of the extractor supply stream which supplies extractant to the extraction section.

3 Claims, 3 Drawing Sheets

METHOD FOR PREPARING 1,3,5-TRIOXANE

TECHNICAL FIELD

The present invention relates to a method of preparing 1,3,5-trioxane using a reaction distillation tower including a reactor and a distillation tower provided with a distillation unit and an extraction unit.

BACKGROUND ART

Conventionally, 1,3,5-trioxane is obtained by the cyclization reaction of formaldehyde in the presence of an acid catalyst or a solid acid catalyst. A 1,3,5-trioxane-containing vapor obtained by the cyclization reaction is supplied from a reactor to a distillation tower. The 1,3,5-trioxane-containing vapor boiling in the distillation tower is concentrated and discharged, and then this concentrated 1,3,5-trioxane-containing vapor is extracted with a water-insoluble organic solvent. Further, the 1,3,5-trioxane-containing vapor boiling in the distillation tower may be directly extracted with a water-insoluble organic solvent. In both cases, 1,3,5-trioxane is extracted by both a distillation tower and an extraction tower, and an extracted liquid is converted into a solution containing a small amount of 1,3,5-trioxane by a fractionator, and then the solution is refluxed into the extraction tower.

For example, in the case of JP 1982-200383, a distillation tower and an extraction tower are separately provided in order to prepare 1,3,5-trioxane. 1,3,5-trioxane concentrated at the top of the distillation tower is introduced into the extraction tower, and is then extracted with a water-insoluble organic solvent. This method of preparing 1,3,5-trioxane disclosed in JP 1982-200383 is problematic in that an equipment investment cost excessively increases because a distillation tower and an extraction tower are separately provided in order to prepare 1,3,5-trioxane, in that the preparation efficiency of 1,3,5-trioxane remarkably decreases because a large amount of formaldehyde and 1,3,5-trioxane, other than 1,3,5-trioxane extracted with extractant in the extraction tower, is discharged to the outside of a system, and in that distillation loss increases in the recovery process for recovering and reusing 1,3,5-trioxane.

DISCLOSURE

Technical Problem

The present invention intends to provide a method of preparing 1,3,5-trioxane using a reaction distillation tower including a reactor and a distillation tower provided with integrally-formed distillation and extraction units, which can improve the preparation efficiency of 1,3,5-trioxane.

Technical Solution

An aspect of the present invention provides a method of preparing 1,3,5-trioxane using a reaction distillation tower including a reactor 10 and a distillation tower 20 provided with integrally-formed distillation and extraction units 21 and 22, wherein, at the time of extracting 1,3,5-trioxane from the extraction unit 22, a part of a water phase, which is separated from a stream discharged from a top of the distillation tower 20, is refluxed to an upper end of an extractant supply stream of the extraction unit 22.

In the method of preparing 1,3,5-trioxane, the concentration of formaldehyde in the water phase separated from the stream discharged from the top of the distillation tower 20 may be 15 wt % or less.

DESCRIPTION OF THE REFERENCE NUMERALS IN THE DRAWINGS

Figure 1:
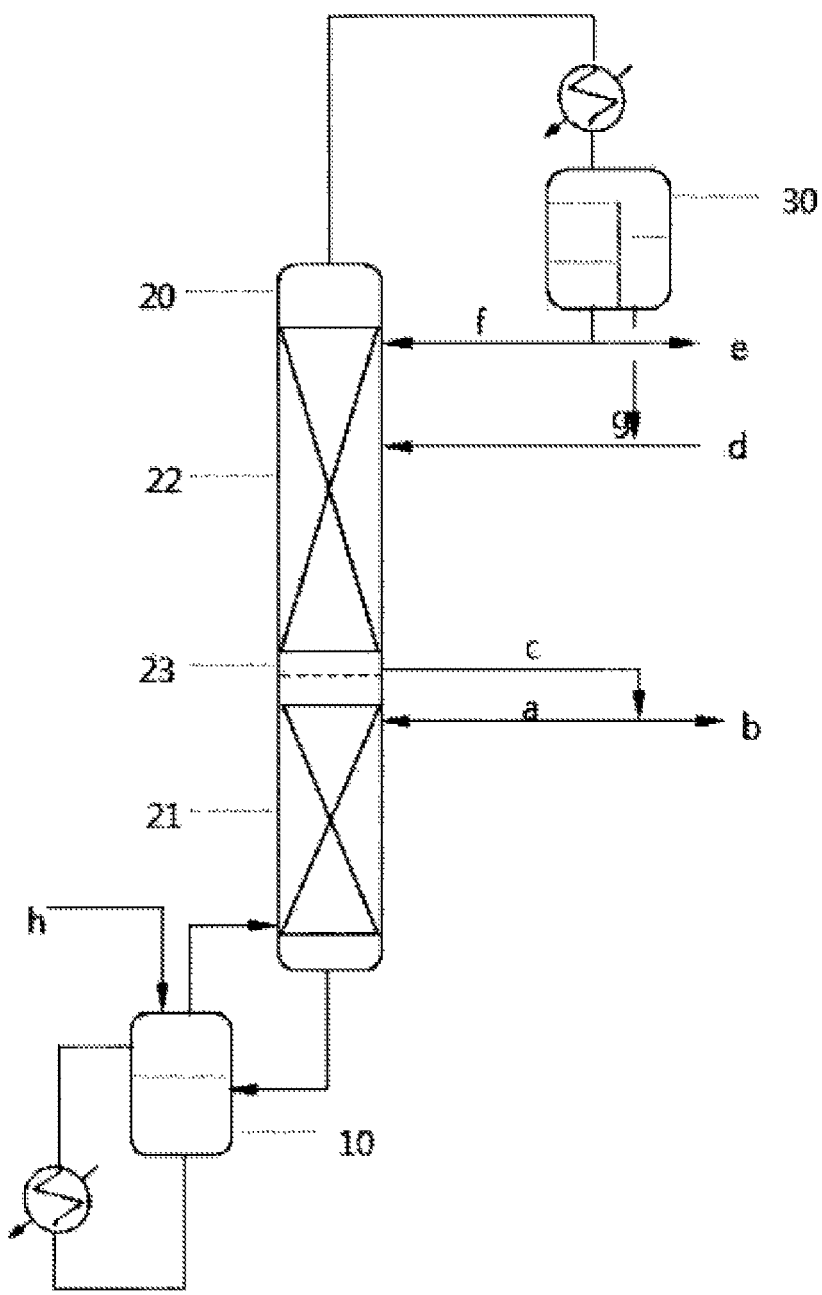
FIG. 1 is a schematic view showing a reaction distillation tower used in preparing 1,3,5-trioxane according to the present invention, the reaction distillation tower including a distillation tower provided with integrally-formed distillation and extraction units, wherein a part of a water phase, which is separated from a stream discharged from the top of the distillation tower, is refluxed to the upper end of an extractant supply stream of the extraction unit.

10: Reactor
20: Distillation tower
21: Distillation unit
22: Extraction unit
23: Side cut unit (Chimney-tray unit)
24: Distillation tower
25: Extraction tower
30: Decanter

BEST MODE

Hereinafter, the present invention will be described in detail.

An embodiment of the present invention provides a method of preparing 1,3,5-trioxane using a reaction distillation tower including a reactor and a distillation tower provided with integrally-formed distillation and extraction units, wherein, at the time of extracting 1,3,5-trioxane from the extraction unit, a part of a water phase, which is separated from a stream discharged from the top of the distillation tower, is refluxed to the upper end of an extractant supply stream of the extraction unit.

Particularly, an embodiment of the present invention provides a method of preparing 1,3,5-trioxane, wherein a stream discharged from a side cut unit of a distillation tower including a distillation unit and an extraction unit is separated into an oil phase and a water phase, and then the water phase is returned to the distillation unit of the distillation tower, and simultaneously water supplied to the reactor is azeotropically boiled with an extractant in the extraction unit for extracting 1,3,5-trioxane, discharged from the top of the distillation tower and then separated into a water phase and an oil phase, and then a part of the water phase is discharged to the outside of a system, and the remaining water phase is refluxed into the upper end of an extractant supply stream, so the concentration of formaldehyde formed in the extraction unit is lowered, and thus the amount of formaldehyde discharged to the outside of the system without participating in a reaction can be reduced, thereby increasing the preparation efficiency of 1,3,5-trioxane.

Generally, a method of preparing 1,3,5-trioxane using a reaction distillation tower including a reactor and a distillation tower provided with a distillation unit and an extraction unit includes the processes of:

(1) producing a 1,3,5-trioxane-containing vapor from formaldehyde in the presence of an acid catalyst;

(2) distilling and extracting the 1,3,5-trioxane-containing vapor to separate 1,3,5-trioxane;

(3) separating the 1,3,5-trioxane-containing vapor into a water phase and an oil phase and then returning the water phase to the distillation tower; and (4) discharging water supplied to the reactor to the outside of a system.

The method of preparing 1,3,5-trioxane according to the present invention is characterized in that (i) distillation and extraction units included in a distillation tower are integrated with each other, and (ii) although the water phase discharged from the top of the distillation tower may be discharged to the outside of a system or may be refluxed into the extraction unit, this water phase is refluxed into the upper end of an extractant supply stream when the water phase is refluxed into the extraction unit.

That is, in the method of preparing 1,3,5-trioxane according to the present invention, the processes (2), (3) and (4) are realized by one distillation tower including a distillation unit and an extraction unit. Further, in this method, in the process (4) of discharging water supplied to the reactor to the outside of a system, in order to minimize the discharge of formaldehyde, the water supplied to the reactor is azeotropically boiled with an extractant in the extraction unit of the distillation tower, discharged from the top of the distillation tower and then separated into a water phase and an oil phase, and then a part of the water phase is discharged to the outside of a system, and the remaining water phase is refluxed into the upper end of an extractant supply stream, so the concentrate of formaldehyde formed in the extraction unit is lowered, with the result that the amount of formaldehyde discharged to the outside of the system without participating in a reaction can be reduced, thereby increasing the preparation efficiency of 1,3,5-trioxane.

Hereinafter, the present invention will be described in more detail with reference to the accompanying drawings.

In the reactor 10, 1,3,5-trioxane is prepared from formaldehyde in the presence of an acid catalyst. Formaldehyde, which is a raw material of 1,3,5-trioxane, is supplied into the reactor 10, and is then heated in the presence of an acid catalyst to synthesize 1,3,5-trioxane.

Formaldehyde, which is a raw material used to synthesize 1,3,5-trioxane, may exist in the form of formaldehyde gas, an aqueous formaldehyde solution, para-formaldehyde or the like. Preferably, an aqueous formaldehyde solution may be used in terms of tractability.

The acid catalyst may be a homogeneous catalyst. A solid acid catalyst may be used as the acid catalyst. Examples of the acid catalyst may include mineral acids, such as sulfuric acid, phosphoric acid and the like; strong organic acids, such as sulfonic acid, phosphonic acid, trifluoroacetic acid and the like; solid acids, such as a strong-acid cation exchanger, zeolite, silica, alumina, active white clay and the like; and heteropoly acids, such as phosphomolybdic acid, phosphotungstenic acid and the like.

1,3,5-trioxane synthesized in the reactor 10 is supplied to the distillation tower 20 together with supplied water and formaldehyde. Specifically, a 1,3,5-trioxane-containing vapor is supplied to the distillation tower 20. The 1,3,5-trioxane-containing vapor includes 1,3,5-trioxane, formaldehyde and water.

In the distillation tower 20, the 1,3,5-trioxane-containing vapor supplied from the reactor 10 is distilled and extracted to separate 1,3,5-trioxane.

For this purpose, the distillation tower 20 includes a distillation unit 21 located at the lower portion thereof and an extraction unit 22 located at the upper portion thereof. The distillation tower 20 may be provided with an inner-structured side cut unit 23 such as a chimney tray or a column adaptor between the distillation unit 21 and the extraction unit 22.

The 1,3,5-trioxane-containing vapor supplied from the reactor 10 is introduced into the distillation unit 21 located at the lower portion of the distillation tower 20.

In the distillation unit 21, as described above, the 1,3,5-trioxane-containing vapor supplied from the reactor 10 is introduced into the lower end of the distillation unit 21, the water phase (a) returning to the distillation unit 21 from the side cut unit 23 of the distillation tower 20 condenses the rising 1,3,5-trioxane-containing vapor, and a part of the 1,3,5-trioxane-containing vapor is supplied from the distillation unit 21 to the extraction unit 22 via the side cut unit 23. The formaldehyde included in the water phase (a) returning to the distillation unit 21 can be reused in the reactor 10 for synthesizing 1,3,5-trioxane.

In the extraction unit 22, 1,3,5-trioxane is separated from the 1,3,5-trioxane-containing vapor supplied from the distillation unit 21. For this purpose, an extractant is supplied into the extraction unit 22 through an extractant supply stream (d). A part of the extractant supplied through the extractant supply stream (d) is azeotropically boiled with water, discharged from the top of the distillation tower 20, and then returns to the extraction unit 22 through a extractant return stream (g).

Further, the 1,3,5-trioxane-containing liquid phase separated from the extraction unit 22 is discharged to a stream (c) through the side cut unit 23 of the distillation tower 20, and is then separated into an oil phase (b) and a water phase (a). Here, the water phase (a) may return to the distillation unit. In this case, the stream (c) may include 1,3,5-trioxane, formaldehyde, an extractant and water.

In the extraction unit 22, an extractant is externally supplied thereinto through the extractant supply stream (d) in order to separate 1,3,5-trioxane. A part of the extractant for separating 1,3,5-trioxane may be an organic solvent that can be azeotropically boiled with water. Specific examples of the organic solvent may include halogenated aliphatic hydrocarbons such as methylene chloride, chloroform, carbon tetrachloride, ethylene chloride and the like; halogenated aromatic hydrocarbons such as chlorobenzene, o-chlorobenzene and the like; and aromatic hydrocarbons such as benzene, toluene and the like. Among these organic solvents, benzene can be preferably used.

The extractant supplied to the extraction unit 22 and the water introduced into the extraction unit 22 through the reactor 10 and the distillation unit 21 are discharged from the top of the distillation tower 20 by azeotropic distillation, and, in this procedure, a formaldehyde-containing vapor may also be discharged from the top of the distillation tower 20 together with the extractant and the water.

Therefore, in the water discharged from the top of the distillation tower 20, the same amount of a water phase as that of water introduced into the reactor 10 may be discharged to the outside through a stream (e), and residual water phase may return to the top of the distillation tower 20 through a stream (f) in order to lower the concentration of formaldehyde discharged from the top thereof together with the water phase in the process of azeotropic distillation.

Consequently, a part of the water phase discharged from the top of the distillation tower 20 together with the extractant returns to the extraction unit 22 of the distillation tower 20 through the stream (f), so the amount of formaldehyde discharged to the outside through the top of the distillation tower 20 can be reduced, and thus the preparation efficiency of 1,3,5-trioxane can be increased.

The oil phase stream (g) and the water phase streams (e and f) separated from the stream discharged from the top of the distillation tower 20 may include other materials, such as methanol, formic acid, methylal, methyl formate and the like.

MODE FOR INVENTION

Hereinafter, the present invention will be described in more detail with reference to the following Examples. However, the scope of the present invention is not limited to these Examples.

Example 1

1,3,5-trioxane was prepared using a reaction distillation tower shown in FIG. 1.

The reaction distillation tower includes a distillation tower 20 provided with a distillation unit 21 (diameter 30 mm, 15 stages, bubble-cap tray), an extraction unit 22 (diameter 50 mm, 20 stages, bubble-cap tray) and a side cut unit 23 (one stage, chimney tray) disposed between the distillation unit 21 and the extraction unit 22, a reactor 10 (volume 5 L, provided with a heating unit) and a decanter (volume 1.5 L).

An aqueous solution containing formaldehyde in a concentration of 65.0 wt % was supplied to the reactor 10 at a flow rate of 400 g/hr, and the concentration of sulfuric acid in a reaction solution was set to 2.0 wt %. A 1,3,5-trioxane-containing vapor produced by steam heating of 1400 g/hr was supplied to the distillation unit 21 of the distillation tower 20.

The 1,3,5-trioxane-containing vapor was supplied to the extraction unit 22, and simultaneously benzene was supplied to the extraction unit 22 as an extractant through a stream (d).

The 1,3,5-trioxane-containing vapor supplied to the distillation unit 21 was introduced into the extraction unit 22, was discharged from the side cut unit 23 to a stream (c) together with benzene supplied to the extraction unit 22, and was then phase-separated into a water phase (a) and an oil phase (b). Then, the oil phase (b) was balanced with benzene supplied to the extraction unit 22 by adjusting the flow rate of the oil phase (b) to 620 g/hr.

The water phase (a) separated from the side cut unit 23 of the distillation tower 20 was refluxed into the distillation unit 21 in order to maintain an interface.

A part of benzene supplied through the extractant supply stream (d) was azeotropically boiled with water by the steam supplied to the reactor 10, and was then discharged from the top of the distillation tower 20. The discharged benzene was reused through a stream (g). A part of water supplied to the reactor 10 was discharged through a stream (e), and residual water was refluxed to the top of the distillation tower 20 through a stream (f).

For this purpose, in the stream (e), the flow rate of water was maintained at 162 g/hr, and, in the stream (f), the flow rate thereof was maintained at 300 g/hr. After 20 hours from operation start, the composition obtained from the top of the distillation tower 20 includes 84.0 wt % of water, 11.6 wt % of formaldehyde and 4.4 wt % of a residue.

Comparative Example 1

Figure 2:
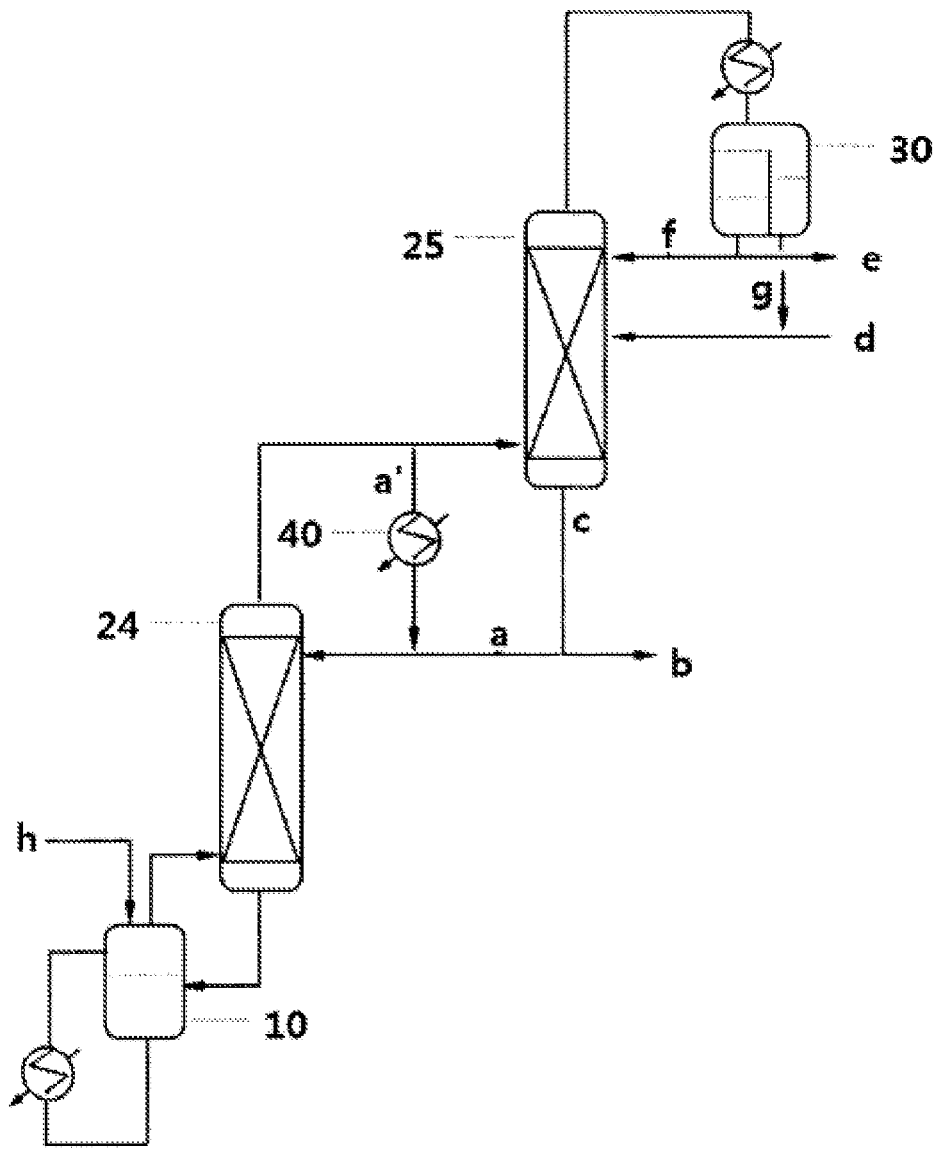
FIG. 2 is a schematic view showing a reaction distillation tower used in preparing 1,3,5-trioxane, wherein the reaction distillation tower is configured such that a distillation tower and an extraction tower is separately provided.
Figure 3:
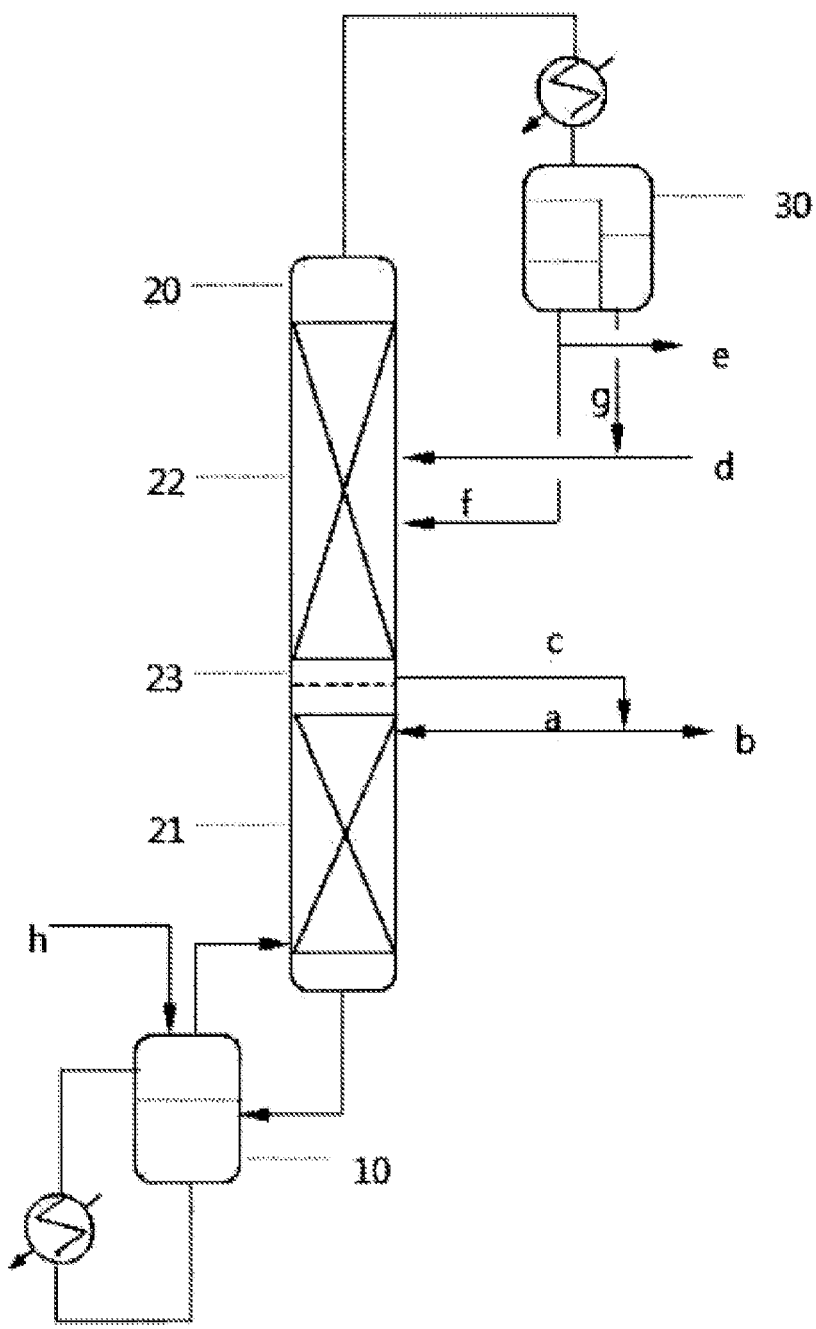
FIG. 3 is a schematic view showing a reaction distillation tower used in preparing 1,3,5-trioxane according to the present invention, the reaction distillation tower including a distillation tower provided with integrally-formed distillation and extraction units, wherein a part of a water phase, which is separated from a stream discharged from the top of the distillation tower, is refluxed to the lower end of an extractant supply stream of the extraction unit.

1,3,5-trioxane was prepared using a distillation tower 24 (diameter 30 mm, 15 stages, bubble-cap tray), an extraction tower 25 (diameter 50 mm, 20 stages, bubble-cap tray), a reactor 10 (volume 5 L, provided with a heating unit), a decanter (volume 1.5 L) and a condenser 40 for condensing a part of a vapor discharged from the distillation tower, as shown in FIG. 2 in which the distillation tower 24 and the extraction tower 25 are provided by separating the distillation unit 21 and the extraction unit 22 from the distillation tower 20 shown in FIG. 1.

An aqueous solution containing formaldehyde in a concentration of 65.0 wt % was supplied to the reactor 10 at a flow rate of 400 g/hr, and the concentration of sulfuric acid in a reaction solution was set to 2.0 wt %. A 1,3,5-trioxane-containing vapor produced by steam heating of 1400 g/hr was supplied to the distillation tower 24. A part of the 1,3,5-trioxane-containing vapor discharged from the distillation tower 24 returned to the top of the distillation tower 24 through a stream (a'), and the 1,3,5-trioxane-containing vapor was supplied to the extraction tower 25, and simultaneously benzene was supplied to the extraction tower 25 as an extractant through a stream (d).

The 1,3,5-trioxane-containing vapor supplied from the top of the distillation tower 24 to the bottom of the extraction tower 25 was discharged from the bottom of the extraction tower 25 through a stream (c) together with benzene supplied to the extraction tower 25, and was then phase-separated into a water phase (a) and an oil phase (b). Then, the oil phase (b) was balanced with benzene supplied to the extraction tower 25 by adjusting the flow rate of the oil phase (b) to 600 g/hr.

The water phase (a) separated from the bottom of the extraction tower 25 was refluxed into the distillation tower 24 in order to maintain an interface.

A part of benzene supplied through the extractant supply stream (d) was azeotropically boiled with water by the steam supplied to the reactor 10, and was then discharged from the top of the extraction tower 25. The discharged benzene was reused through a stream (g). A part of water supplied to the reactor 10 was discharged through a stream (e), and residual water was refluxed to the top of the extraction tower 25 through a stream (f).

A part of the 1,3,5-trioxane-containing vapor discharged from the distillation tower 24 was condensed, and then returned to the top of the distillation tower 24. For this purpose, in the stream (e), the flow rate of water was maintained at 175 g/hr, and, in the stream (f), the flow rate thereof was maintained at 156 g/hr. After 20 hours from operation start, the waster phase (e) obtained from the top of the extraction tower 25 includes formaldehyde in a concentration of 19.5 wt %.

Comparative Example 2

1,3,5-trioxane was prepared in the same condition as in Example 1, except that the water phase separated from the top of the distillation tower 20 was returned to the to lower end of an extractant supply stream (e) through a stream (f).

For this purpose, in the stream (e), the flow rate of water was maintained at 162 g/hr, and, in the stream (f), the flow rate thereof was maintained at 300 g/hr. After 20 hours from operation start, the waster phase (e) obtained from the top of the extraction unit 22 of the distillation tower 20 includes formaldehyde in a concentration of 32.0 wt %.

In each of the 1,3,5-trioxane preparation processes of Example 1 and Comparative Examples 1 and 2, the concentration of formaldehyde in the extraction unit 22 was analyzed using the following method.

The concentration of formaldehyde in the extraction unit 22 was analyzed using gas chromatography (detector TCD, separation tube APS-201 20% Flusin T 30-60 mesh 4 m). 1 μL of a sample was taken by a 10 μL syringe, and was then analyzed by gas chromatography under conditions of an inlet temperature of 170° C., a detector temperature of 150° C., a separation tube temperature of 110° C. and a helium gas flow rate of 20 mL/min.

TABLE 1

| | Unit | Ex. 1 | Comp. Ex. 1 | Comp. Ex. 2 |
|---|---|---|---|---|
| Formaldehyde ($\alpha$) supplied into system | g/hr | 260.0 | 260.0 | 260.0 |
| Formaldehyde ($\beta$) discharged to the outside of system | g/hr | 18.8 | 30.4 | 51.8 |
| Ratio ($\beta/\alpha$) of Formaldehyde ($\alpha$) to Formaldehyde ($\beta$) | % | 7.2 | 11.7 | 19.9 |
| concentration of formaldehyde in water phase (e, f) discharged from top of extraction unit 22 or top of extraction tower 25 | wt % | 11.6 | 19.5 | 32.0 |
| Configuration of distillation tower | | single distillation tower | one distillation tower and one extraction tower | single distillation tower |
| Position of water phase stream (f) refluxed to system without being discharged to the outside of system | | extractant supply stream (d) is connected with top of extraction unit | extractant supply stream (d) is connected with top of extraction tower | extractant supply stream (d) is connected with lower portion of extraction unit |

As the results of measuring the concentration of formaldehyde in the extraction unit 22 in each of the 1,3,5-trioxane preparation processes of Example 1 and Comparative Examples 1 and 2, as given in Table 1 above, it can be ascertained that, when a distillation tower including integrally-formed distillation and extraction units was used (Example 1), the amount of formaldehyde discharged to the outside of a system was small compared to when a distillation tower including separately-formed distillation and extraction units was used (Comparative Example 1).

Further, it can be ascertained that, when the water phase discharged from the top of the distillation tower and then phase-separated was returned to the upper end of the extractant supply stream (Example 1), the amount of formaldehyde discharged to the outside of a system was small compared to when this water phase was returned to the to lower end of the extractant supply stream (Comparative Example 2).

Consequently, it can be ascertained that, when 1,3,5-trioxane is prepared by returning the water phase discharged from the top of the distillation tower and then phase-separated to the upper end of the extractant supply stream using the distillation tower including integrally-formed distillation and extraction units, the amount of formaldehyde (raw material) discharged to the outside of a system can be reduced, and thus the preparation efficiency of 1,3,5-trioxane can be improved.

The invention claimed is:

1. A method of preparing 1,3,5-trioxane using a distillation apparatus comprising a reactor 10, a distillation tower 20, and a decanter 30, wherein the distillation tower 20 comprises integrally-formed distillation and extraction units 21 and 22, said extraction unit being provided on the top of the distillation unit,
said method comprising
preparing a first 1,3,5-trioxane-containing vapor from formaldehyde in the reactor 10;
distilling the first 1,3,5-trioxane-containing vapor in the distillation unit 21 to give a second distilled 1,3,5-trioxane-containing vapor; and
introducing the second distilled 1,3,5-trioxane-containing vapor into the extraction unit 22 and subjecting the second distilled 1,3,5-trioxane-containing vapor to an extraction with an organic solvent to produce a third 1,3,5-trioxane-containing vapor, said third vapor containing a water phase and an oil phase, and said organic solvent being capable of being azeotropically boiled with water;
wherein the distillation and extraction are performed in the distillation tower,
wherein the third 1,3,5-trioxane-containing vapor is discharged from a top of the distillation tower 20 and separated into the water phase and the oil phase, and
wherein a part of the water phase is returned to the extraction unit 22 at an upper end of the extraction unit.

2. The method of preparing 1,3,5-trioxane according to claim 1, wherein the concentration of formaldehyde in the water phase discharged from the top of the distillation tower 20 is 15 wt % or less.

3. The method of preparing 1, 3, 5-trioxane according to claim 1, wherein the extraction unit 22 is supplied with the organic solvent from an external source and wherein the part of the water phase separated from the third 1,3,5-trioxane-containing vapor is introduced into a flow of the organic solvent from the external source to the extraction unit 22.

* * * * *